United States Patent
Javet et al.

(10) Patent No.: US 7,413,578 B2
(45) Date of Patent: Aug. 19, 2008

(54) COLORANTS COMPRISING CATIONIC AZACYANINE DYES

(75) Inventors: Manuela Javet, Marly (CH); Catherine Müller, Marly (CH); Anita Roulin, Villarlod (CH); Cécile Pasquier, Marly (CH)

(73) Assignee: The Procter & Gamble Company, Cincinnati, OH (US)

( * ) Notice: Subject to any disclaimer, the term of this patent is extended or adjusted under 35 U.S.C. 154(b) by 122 days.

(21) Appl. No.: 11/339,350

(22) Filed: Jan. 25, 2006

(65) Prior Publication Data

US 2007/0000071 A1 Jan. 4, 2007

(51) Int. Cl.
*A61Q 5/10* (2006.01)
*C07D 293/00* (2006.01)
(52) U.S. Cl. .................. 8/405; 8/406; 8/429; 8/688; 8/689; 8/690; 8/691; 548/100
(58) Field of Classification Search .............. 8/405, 8/406, 429, 688, 689, 690, 691; 548/100
See application file for complete search history.

(56) References Cited

U.S. PATENT DOCUMENTS

| 3,130,197 A | 4/1964 | Seefelder et al. |
| 5,865,855 A | 2/1999 | Doehling et al. |

FOREIGN PATENT DOCUMENTS

| DE | 3929383 A1 | 3/1991 |
| DE | 19618595 A1 | 11/1995 |
| EP | 0285000 A2 | 10/1988 |
| EP | 1433468 A1 | 6/2004 |
| JP | 07-085499 A | 3/1995 |
| JP | 07-126543 A | 5/1995 |
| JP | 10060295 A * | 3/1998 |
| WO | WO-2006/042614 A1 | 4/2006 |

OTHER PUBLICATIONS

STIC Search Report dated Oct. 30, 2007.*
International Search Report for PCT/US2006/002494, Sep. 21, 2006 (6 pages).
Kroeck F. W. et al., "Eine Neue Indolizin-Synthese Mit 2-Acyl-Pyridinen, II Blaue Azacyanine a New Indolizine synhesis with 2-Acylpyridines, II Blue Azacyanines," *Chemische Berichte*, vol. 104, Nr. 5, 1971, pp. 1645-1654, XP009059227.
H. Quast and S. Hunig, *Chem. Ber.*, 101, 435-444 (1968).
K. S. Huang et al., *J. Org. Chem.*, 2001, 66, 1310-1315.

* cited by examiner

*Primary Examiner*—Eisa B Elhilo
(74) *Attorney, Agent, or Firm*—Idris N. McKelvey

(57) ABSTRACT

The present invention relates to agents comprising cationic azacyanine dyes of the formula (I) for coloring keratin fibers, such as, for example, wool, silk or furs and in particular human hair (I)

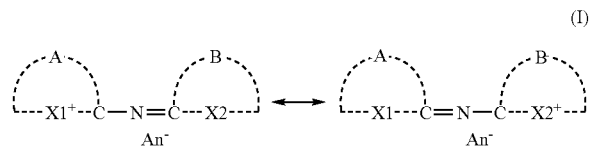

(where X1 is N—R1, O or S and X2 is N—R2, O or S), and to a method of coloring hair with varying degrees of damage.

4 Claims, No Drawings

COLORANTS COMPRISING CATIONIC AZACYANINE DYES

FIELD OF THE INVENTION

The present invention relates to agents comprising cationic azacyanine dyes for coloring keratin fibers, such as, for example, wool, silk, furs or hair and, in particular, human hair.

BACKGROUND OF THE INVENTION

Cationic direct dyes have been known for a long time in hair tints. In oxidative coloring systems, which simultaneously lighten the natural hair melanin during the coloring operation, nitro and azo dyes in particular are used since most other types of dye do not withstand the oxidizing process.

From JP-OS 07-126543 it is known to use certain azacyanines for the surface treatment of optical recording media. It is likewise known from European patent 0285000 to use certain cationic azacyanine dyes for detecting enzymes cleaving peptide bonds.

DETAILED DESCRIPTION OF THE INVENTION

Surprisingly, it has now been found that certain cationic azacyanine dyes permit colorations especially in the yellow and red region and, depending on the substitution pattern, are oxidation-stable and can thus also be used in oxidative coloring systems.

The present application therefore provides (a) an agent for the nonoxidative coloring of keratin fibers, preferably human hair, which is characterized in that it comprises at least one cationic azacyanine dye of the general formula (I);

(b) an agent for the simultaneous lightening and coloring of keratin fibers, preferably human hair, which, besides the dye of the formula (I), comprises an oxidizing agent and is characterized in that it comprises at least one oxidizing-agent-stable cationic azacyanine dye of the general formula (I); and (c) an oxidative colorant for coloring keratin fibers, preferably human hair, based on at least one oxidation dye precursor, which is characterized in that it comprises at least one oxidizing-agent-stable cationic azacyanine dye of the general formula (I);

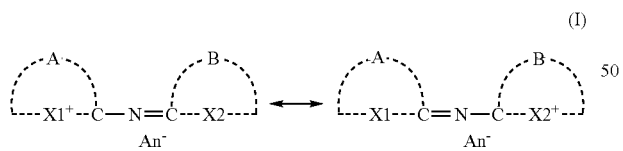

(I)

where X1 is N—R1, O or S and X2 is N—R2, O or S;

A and B are the group required to form an aromatic carbocyclic or heterocyclic (nitrogen, oxygen or sulfur, where up to three heteroatoms may be present), 5- or 6-membered ring to which further carbocyclic or heterocyclic 5- or 6-membered rings may be fused; R1 and R2 independently of one another, may be identical or different and are a substituted or unsubstituted, saturated or unsaturated (C1-C10)-alkyl group, a substituted or unsubstituted aryl group or a substituted or unsubstituted benzyl group, or act as a member of a fused carbocyclic or heterocyclic 5- or 6-membered ring; and An⁻ is an anion.

Radicals R1 and R2 which may be mentioned are, for example, a (C1-C10)-alkyl group substituted by one or more alkoxy groups, hydroxyl groups, carboxamide groups, dialkylamino groups, alkylamino groups, carboxylic ester groups, carboxylic acid groups or sulfonic acid groups; an unsubstituted benzyl group; a benzyl group substituted by one or more alkyl groups, alkoxy groups, alkoxyalkyl groups, hydroxyl groups, hydroxyalkyl groups, carboxamide groups, dialkylamino groups, carboxylic ester groups, alkylcarboxylic ester groups, carboxylic acid groups, alkylcarboxylic acid groups, sulfonic acid groups or halogen atoms (F, Cl, Br, I); or a six-membered or five-membered aromatic carbocyclic or heterocyclic (nitrogen, oxygen or sulfur) ring, which may be unsubstituted or substituted by one or more alkyl groups, alkoxy groups, alkoxyalkyl groups, hydroxyl groups, hydroxyalkyl groups, carboxamide groups, dialkylamino groups, carboxylic ester groups, alkylcarboxylic ester groups, carboxylic acid groups, alkylcarboxylic acid groups, sulfonic acid groups or halogen atoms (F, Cl, Br, I).

Anions An— which may be specified are, for example, organic or inorganic acid anions, such as, for example, halides (chloride, bromide, iodide), sulfates, acetates, formate, propionate, lactates, perchlorate, hexafluoro-phosphate, tetrafluoroborate or tetraphenylborate.

It is a common feature of all of the structures of the general formula (I) that in the two mesomeric structures the group X1 or X2 carrying the cationic charge is always located on the side of the aza bridge nitrogen that is opposite to the double bond of the aza bridge.

A and B represent the C, N, O or S atoms required for forming the particular carbocyclic or heterocyclic ring system.

The ring system of the first mesomeric structure of the formula (I) located left of the aza bridge preferably has the following structure (where D is the remaining molecular moiety):

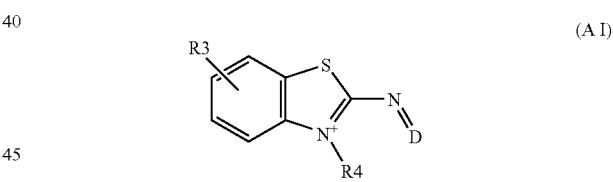

(A I)

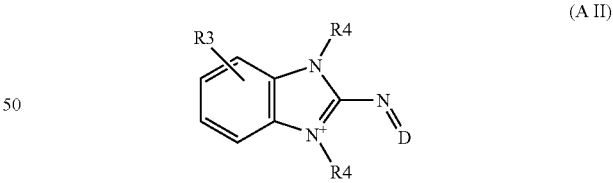

(A II)

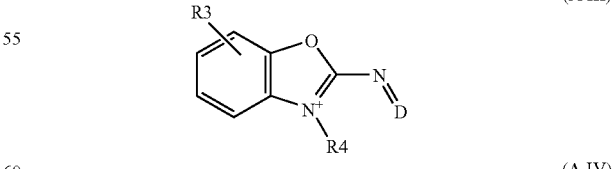

(A III)

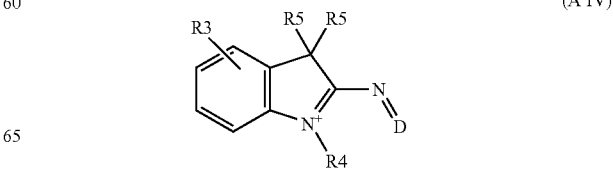

(A IV)

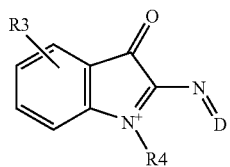 (A V)
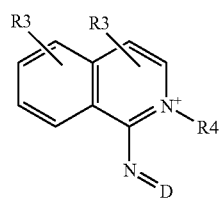 (A VI)
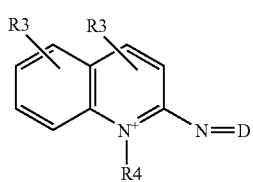 (A VII)
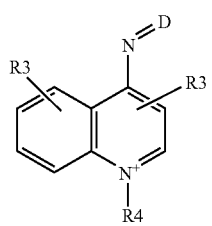 (A VIII)
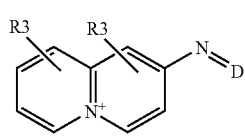 (A IX)
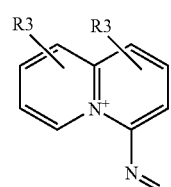 (A X)
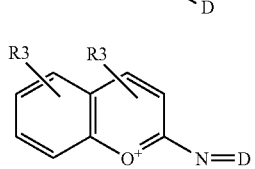 (A XI)
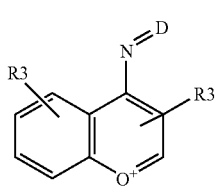 (A XII)
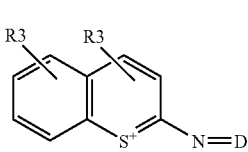 (A XIII)
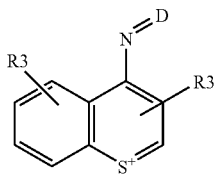 (A XIV)
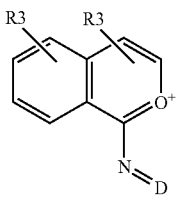 (A XV)
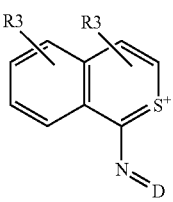 (A XVI)
The ring system referred to above as D and located on the right-hand side of the aza bridge of the first mesomeric limiting structure of formula (I) preferably has the following structure:
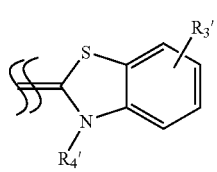 (B I)
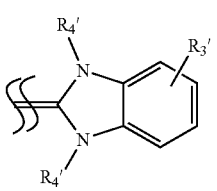 (B II)
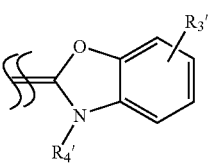 (B III)

-continued

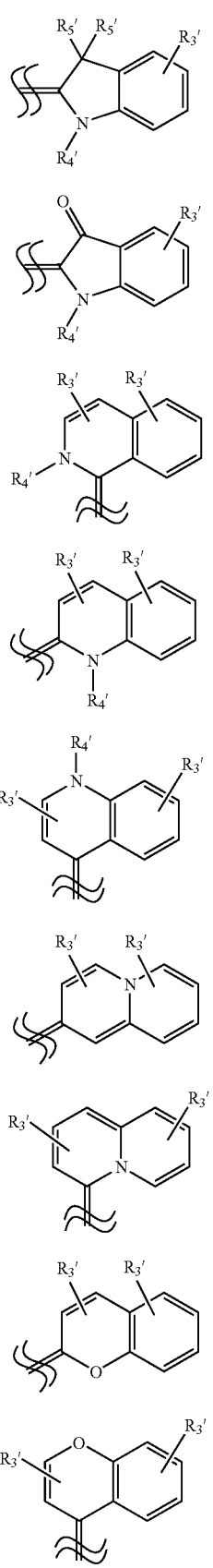

(B IV)
(B V)
(B VI)
(B VII)
(B VIII)
(B IX)
(B X)
(B XI)
(B XII)

-continued

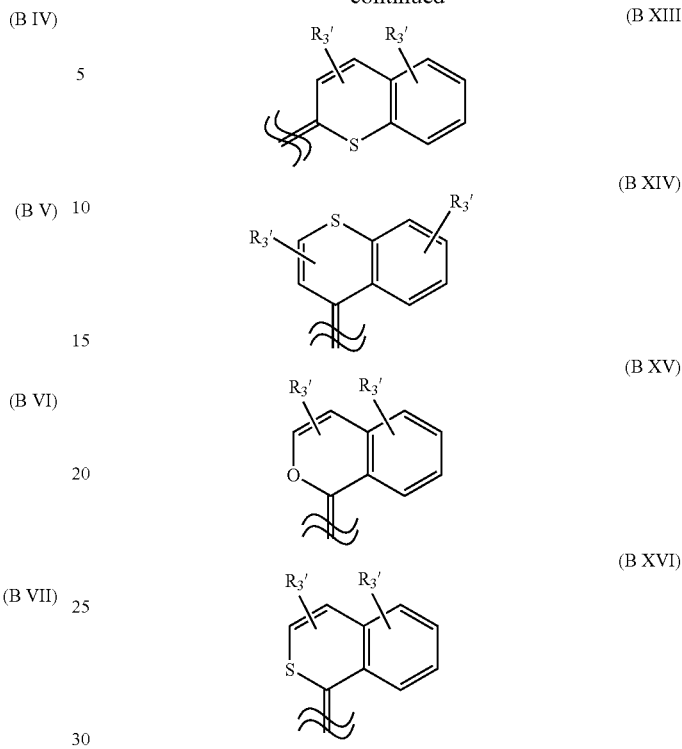

(B XIII)
(B XIV)
(B XV)
(B XVI)

In the abovementioned formulae (AI) to (BXVI) the radicals R3 to R5' have the following meanings:

R3 and R3' may be identical or different and, independently of one another, are hydrogen, an alkyl group, an alkoxy group, an alkoxyalkyl group, a hydroxyl group, a hydroxyalkyl group, an alkylcarboxamide group, an amino group, an alkylamino group, a dialkylamino group, a carboxylic ester group, an alkylcarboxylic ester group, a carboxylic acid group, an alkylcarboxylic acid group, a sulfonic acid group, an alkylsulfonic acid group, a nitro group or a halogen atom (F, Cl, Br, I);

R4 and R4' may be identical or different and, independently of one another, are hydrogen, an unbranched or branched (C1-C10)-alkyl group, which may be unsubstituted or substituted by an alkoxy group, a hydroxyl group, a carboxamide group, a dialkylamino group, an alkylamino group, a carboxylic ester group, a carboxylic acid group or a sulfonic acid group, an unsubstituted benzyl group, a benzyl group substituted by an alkyl group, an alkoxy group, an alkoxyalkyl group, a hydroxyl group, a hydroxyalkyl group, a carboxamide group, a dialkylamino group, a carboxylic ester group, an alkylcarboxylic ester group, a carboxylic acid group, an alkylcarboxylic acid group, a sulfonic acid group or a halogen atom (F, Cl, Br, I), a hydroxyl group, an amino group, an alkoxy group, a substituted phenyloxy group, a dialkylamino group, a substituted benzylamino group, a substituted phenylamino group, an alkylamino group or a six-membered or five-membered aromatic carbocyclic or heterocyclic (nitrogen, oxygen or sulfur) ring which may be unsubstituted or substituted by an alkyl group, an alkoxy group, an alkoxyalkyl group, a hydroxyl group, a hydroxyalkyl group, a carboxamide group, a dialkylamino group, a carboxylic ester group, an alkylcarboxylic ester group, a carboxylic acid group, an alkylcarboxylic acid group, a sulfonic acid group or a halogen atom (F, Cl, Br, I);

R5 and R5' may be identical or different and, independently of one another, are an unbranched or branched (C1-C10)-alkyl group, which may be unsubstituted or substituted by an alkoxy group, a hydroxyl group, a carboxamide group, a dialkylamino group, an alkylamino group, a carboxylic ester group, a carboxylic acid group or a sulfonic acid group, an unsubstituted benzyl group, a benzyl group substituted by an alkyl group, an alkoxy group, an alkoxyalkyl group, a hydroxyl group, a hydroxyalkyl group, a carboxamide group, a dialkylamino group, a carboxylic ester group, an alkylcarboxylic ester group, a carboxylic acid group, an alkylcarboxylic acid group, a sulfonic acid group or a halogen atom (F, Cl, Br, I), or a six-membered or five-membered aromatic carbocyclic ring, which may be unsubstituted or substituted by an alkyl group, an alkoxy group, an alkoxyalkyl group, a hydroxyl group, a hydroxyalkyl group, a carboxamide group, a dialkylamino group, a carboxylic ester group, an alkylcarboxylic ester group, a carboxylic acid group, an alkylcarboxylic acid group, a sulfonic acid group or a halogen atom (F, Cl, Br, I).

The symmetrical azacyanines in which the two ring systems located on the N atom are identical can be prepared, for example, by the method described in DE-A 1 144 280 by condensation of 2-iminobenzothiazoles with a stoichiometric amount of a strong acid at a high temperature. Asymmetrical azacyanines can be prepared using a quinoline derivative (here: 4-chloro-1-ethylquinolinium tetrafluoroborate) and 6-methoxy-3-methylbenzothiazolon-(2)-imine, e.g. analogously to the method described in the publication by H. Quast and S. Hünig, Chem. Ber. 101, 435-444 (1968) for an acridine derivative and 6-methoxy-3-methylbenzothiazolon-(2)-imine.

Symmetrical dyes according to the invention can, for example, have the following resonance structures (II):

The compound colors hair in a cold yellow shade.

In the text below, for the sake of simplicity, only the left-hand of the two mesomeric structures is used to describe the compounds.

The compound of the formula (III) below is one example of an asymmetrical dye according to the invention.

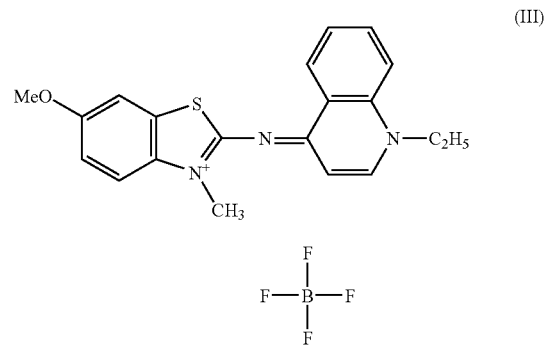

(III)

Depending on the substitution pattern of the dyes of the formula (I), these can also be used in the presence of hydrogen peroxide/alkalinizing agent and even persulfates. For example, the compounds (II) and (III) at a pH of from 3 to 9 (pH adjusted with ammonia, with or without the addition of hydrogen peroxide) produce yellow colorations on bleached hair and are stable to hydrogen peroxide and/or persulfate even at pH 9.

The compound of the formula (IV) produces, likewise on bleached hair, very oxidation-stable yellow colorations:

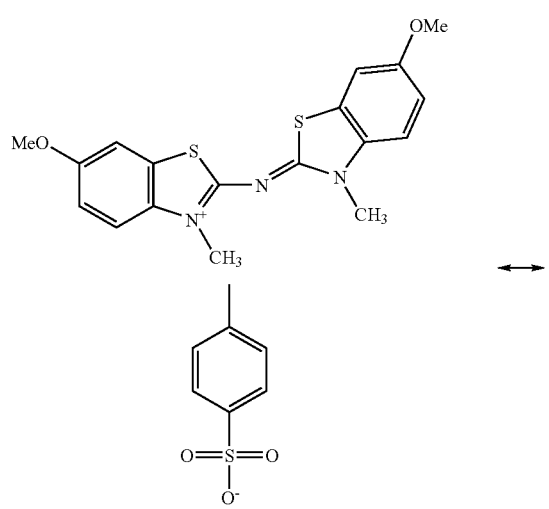 ↔ 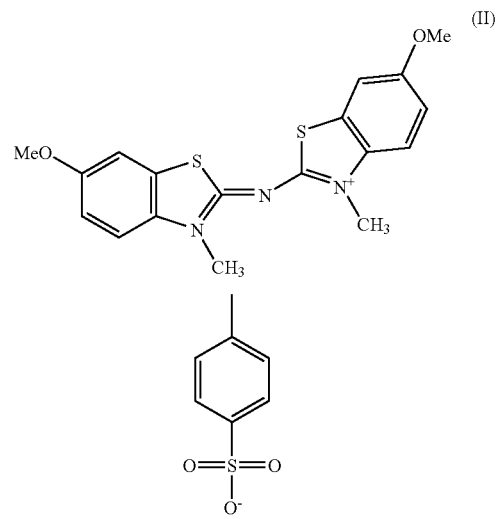

(II)

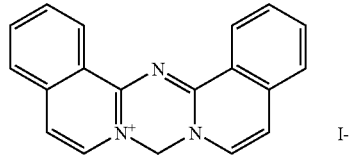

(IV)

The compound of the formula (IV) can be prepared analogously to the method by K. S. Huang, M. J. Haddadin, M. M. Olmstead, M. J. Kurth, J. Org. Chem. 2001, 66, 1310-1315).

Examples of further dyes of the formula (I) according to the invention are

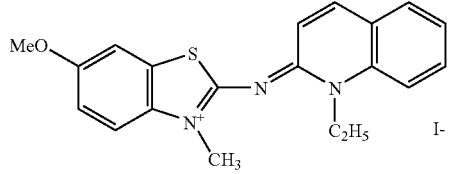

2-{[-1-Ethylquinolinylidene]amino}-6-methoxy-3-methyl-1, 3-benzothiazol-3-iumiodide

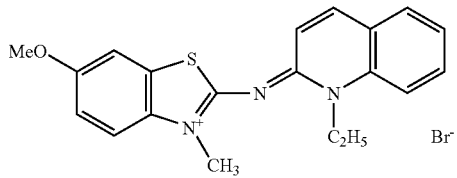

2-{[-1-Ethylquinolinylidene]amino}-6-methoxy-3-methyl-1, 3-benzothiazol-3-iumbromide

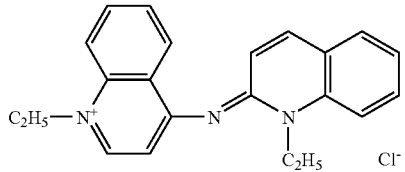

1-Ethyl-4-{[1-ethylquinolinylidene]amino}quinolinium chloride

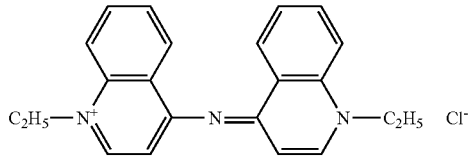

1-Ethyl-4-[(1-ethyl-4(1H)-quinolinylidene)amino]quinolinium chloride

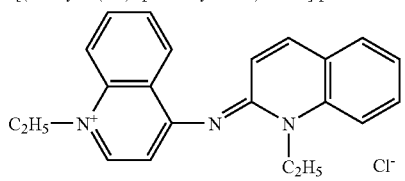

1-Ethyl-4-{[1-ethylquinolinylidene]amino}quinolinium chloride

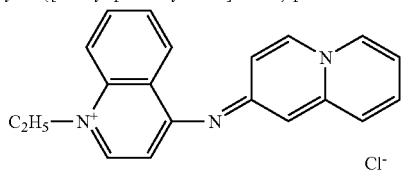

1-Ethyl-4-[2H-quinolizin-2-ylidenamino]quinolinium chloride

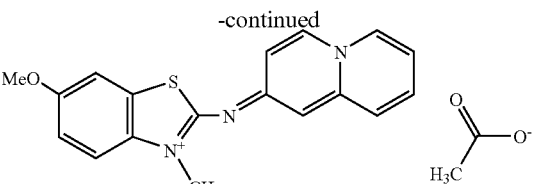

6-Methoxy-3-methyl-2-[2H-quinolizin-2-ylidenamino]-1, 3-benzothiazol-3-iumacetate

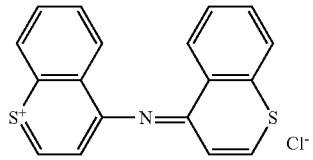

4-(4H-Thiochromen-4-ylidenamino)thiochromenium chloride

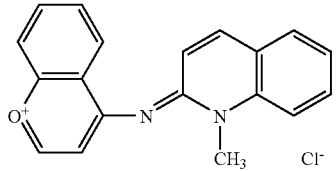

4-{[1-Ethylquinolinylidene]amino}chromenium chloride

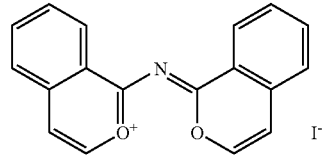

1-[1H-Isochromen-1-ylidenamino]isochromenium iodide

The dyes of the formula (I) are used in the colorant in a total amount of from 0.01 to 15 percent by weight, preferably from 0.05 to 10 percent by weight.

To extend the color palette, besides the dyes of the general formula (I), further natural or synthetic nonoxidative dyes may additionally be present in the colorant according to the invention. Natural dyes which may be specified are plant dyes, such as, for example, henna or indigo, while the synthetic nonoxidative dyes may be azo dyes, triphenylmethane dyes, quinone dyes and in particular nitro dyes, such as, for example, 1,4-bis[(2-hydroxyethyl)amino]-2-nitrobenzene, 1-(2-hydroxyethyl)amino-2-nitro-4-[di(2-hydroxyethyl)amino]benzene, (HC Blue No. 2), 1-amino-3-methyl-4-[(2-hydroxyethyl)amino]-6-nitrobenzene, (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene, (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethylaminobenzoic acid (HC Blue No. 13), 1-(2-aminoethylamino)-4-[di(2-hydroxyethyl)amino]-2-nitrobenzene, 4-(di(2-hydroxyethyl)amino)-2-nitro-1-phenylaminobenzene, 1-amino-4-[(2-hydroxyethyl)amino]-2-nitrobenzene (HC Red No. 7), 2-amino-4,6-dinitrophenol, 1,4-diamino-2-nitrobenzene (CI76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-((2-hydroxyethyl)methylamino)-1-(methylamino)-2-nitrobenzene, 1-amino-4-((2,3-dihydroxypropyl)amino)-5-methyl-2-nitrobenzene, 1-amino-4-(methylamino)-2-nitrobenzene, 4-amino-2-nitro-1-((prop-2-en-1-yl)amino)benzene, 4-amino-3-nitrophenol, 4-[(2-hydroxyethyl)amino]-3-nitrophenol, 4-[(2-nitrophenyl)amino]phenol (HC Orange No. 1), 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene, (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophenol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-((2-hydroxyethyl)amino)-2-nitropyridine, 3-amino-6-((2-hydroxyethyl)amino)-2-nitropyridine, 3-amino-6-(ethylamino)-2-nitropyridine, 3-((2-hydroxyethyl)amino)-6-(methylamino)-2-nitropyridine, 3-amino-6-(methylamino)-2-nitropyridine, 6-(ethylamino)-3-((2-hydroxyethyl)amino)-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (CI76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene, (HC Yellow No. 4), 1-[(2-hydroxyethyl)amino]-2-nitrobenzene (HC Yellow No. 2), 2-(di(2-hydroxyethyl)amino)-5-nitrophenol, 2-[(2-hydroxyethyl)amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride, (HC Yellow No. 9), 1-[(2-ureidoethyl)amino]-4-nitrobenzene, 4-[(2,3-dihydroxypropyl)amino]-3-nitro-1-trifluoromethylbenzene, (HC Yellow No. 6), 1-chloro-2,4-bis[(2-hydroxyethyl)amino]-5-nitrobenzene (HC Yellow No. 10), 1-amino-4-((2-aminoethyl)amino)-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene, (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 3-((2-hydroxyethyl)amino)-4-methyl-1-nitrobenzene, 4-chloro-3-((2-hydroxyethyl)amino)-1-nitrobenzene, 2,4-dinitro-1-hydroxynaphthalene, 1,4-di[(2,3-dihydroxypropyl)amino]-9,10-anthraquinone, 1,4-di[(2-hydroxyethyl)amino]-9,10-anthraquinone (CI61545, Disperse Blue 23), 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-amino-4-hydroxy-9,10-anthraquinone (CI60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-dioxo-3,5,6,8-tetrahydroxy-2-anthracenecarboxylic acid (CI75470, Natural Red 4), 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)-amino]-9,10-anthraquinone (CI62500, Disperse Blue No. 7, Solvent Blue No. 69), 1,4-diamino-9,10-anthraquinone (CI61100, Disperse Violet No. 1), 1-amino-4-(methylamino)-9,10-anthraquinone (CI61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, N-(6-((3-chloro-4-(methylamino)phenyl)imino)-4-methyl-3-oxo-1,4-cyclohexadien-1-yl)urea (HC Red No. 9), 2-((4-(di(2-hydroxy-ethyl)amino)phenyl)amino)-5-((2-hydroxyethyl)amino)-2,5-cyclohexadiene-1,4-dione (HC Green No. 1), 5-hydroxy-1,4-naphthoquinone (CI75500, Natural Brown No. 7), 2-hydroxy-1,4-naphthoquinone (CI75480, Natural Orange No. 6), 1,2-dihydro-2-(1,3-dihydro-3-oxo-2H-indol-2-ylidene)-3H-indol-3-one (CI73000), 1,3-bis(dicyanomethylene)indane, 1-[di(2-hydroxyethyl)amino]-3-methyl-4-[(4-nitrophenyl)azo]benzene (CI11210, Disperse Red No. 17), 1-[di(2-hydroxyethyl)amino]-4-[(4-nitrophenyl)azo]benzene (Disperse Black No. 9), 4-[(4-aminophenyl)azo]-1-[di(2-hydroxyethyl)amino]-3-methylbenzene, (HC Yellow No. 7), 2,6-diamino-3-[(pyridin-3-yl)azo]pyridine, 2-((4-(acetylamino)phenyl)azo)-4-methylphenol (CI11855; Disperse Yellow No. 3) or 2-((4-(ethyl(2-hydroxyethyl)amino)-2-methylphenyl)azo)-5-nitro-1,3-thiazole (CI111935; Disperse Blue No. 106).

Furthermore, further basic (=cationic) dyes may also additionally be present, for example 9-(dimethylamino)benzo[a]phenoxazin-7-ium chloride (CI51175; Basic Blue No. 6), di[4-(diethylamino)phenyl][4-(ethylamino)naphthyl]carbenium chloride (CI42595; Basic Blue No. 7), di(4-(dimethylamino)phenyl)(4-(methylphenylamino)naphthalen-1-yl)carbenium chloride (CI42563; Basic Blue No. 8), 3,7-di(dimethylamino)phenothiazin-5-ium chloride (CI52015; Basic Blue No. 9), di[4-(dimethylamino)phenyl][4-(phenylamino)naphthyl]carbenium chloride (CI44045; Basic Blue No. 26), 2-[(4-(ethyl(2-hydroxyethyl)amino)phenyl)azo]-6-methoxy-3-methylbenzothiazolium methylsulfate (CI11154; Basic Blue No. 41), Basic Blue No. 77, 8-amino-2-bromo-5-hydroxy-4-imino-6-[(3-(trimethylammonio)phenyl)amino]-1(4H)-naphthalenone chloride (CI56059; Basic Blue No. 99), bis[4-(dimethylamino)phenyl][4-(methylamino)phenyl]carbenium chloride (CI42535; Basic Violet No. 1), tri(4-amino-3-methylphenyl)carbenium chloride (CI42520; Basic Violet No. 2), tris[4-(dimethylamino)phenyl]carbenium chloride (CI42555; Basic Violet No. 3), 2-[3,6-(diethylamino)dibenzopyranium-9-yl]benzoyl chloride (CI45170; Basic Violet No. 10), di(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethyl-ammonio)-2-naphthol chloride (CI12250; Basic Brown No. 16), 3-[(4-amino-2,5-dimethoxyphenyl)azo]-N,N,N-trimethylbenzenaminium chloride (CI112605, Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (CI12251; Basic Brown No. 17), 2-((4-aminophenyl)azo)-1,3-dimethyl-1H-imidazol-3-ium chloride (Basic Orange No. 31), 3,7-diamino-2,8-dimethyl-5-phenylphenazinium chloride (CI50240; Basic Red No. 2), 1,4-dimethyl-5-[(4-(dimethylamino)phenyl)azo]-1,2,4-triazolium chloride (CI11055; Basic Red No. 22), 1,3-dimethyl-2-((4-dimethylamino)phenyl)azo-1H-imidazol-3-ium chloride (Basic Red No. 51), 2-hydroxy-1-[(2-methoxyphenyl)azo]-7-(trimethylammonio)naphthalene chloride (CI12245; Basic Red No. 76), 2-[2-((2,4-dimethoxyphenyl)amino)ethenyl]-1,3,3-trimethyl-3H-indol-1-ium chloride (CI48055;

Basic Yellow No. 11), 3-methyl-1-phenyl-4-[(3-(trimethylammonio)phenyl)azo]pyrazol-5-one chloride (CI12719; Basic Yellow No. 57), di[4-(dimethylamino)phenyl]iminomethane hydrochloride (CI41000; Basic Yellow No. 2), 1-methyl-4-((methylphenylhydrazono)methyl)pyridinium methylsulfate (Basic Yellow No. 87), bis[4-(diethylamino)phenyl]phenylcarbenium hydrogensulfate (1:1) (CI42040; Basic Green No. 1), di(4-(dimethylamino)phenyl)phenylmethanol (CI42000; Basic Green No. 4), 1-(2-morpholiniumpropylamino)-4-hydroxy-9,10-anthraquinone methylsulfate, 1-[(3-(dimethylpropylaminium)propyl)amino]-4-(methylamino)-9,10-anthraquinone chloride, 1,4-dimethyl-5-[(4-(dimethylamino)phenyl)azo]-1,2,4-triazolium chloride (C.I. 11055; Basic Red 22), 1-methyl-4-{[methyl(phenyl)hydrazono]methyl}pyridinium chloride (Basic Yellow 87), 1-methyl-4-{(E)-[methyl(4-methoxyphenyl)hydrazono]methyl}pyridinium chloride, 1-methyl-4-({methyl[4-methoxyphenyl]hydrazono}methyl)pyridinium methylsulfate (Basic Yellow 91), 2-{[4-(dimethylamino)phenyl]azo}-1,3-dimethyl-1H-imidazol-3-ium chloride (Basic Red 51), 5-{[4-(dimethylamino)phenyl]azo}-1,2-dimethyl-1H-pyrazol-2-ium chloride, 1,3-dimethyl-2-{[4-(methylamino)phenyl]azo}-1H-imidazol-3-ium chloride (Basic Red 109), 2-[(4-aminophenyl)azo]-1,3-dimethyl-1H-imidazol-3-ium chloride, 4-{[4-(dimethylamino)phenyl]azo}-1-methylpyridinium chloride or N,N-dimethyl-4-[(E)(1-oxido-4-pyridinyl)diazenyl]aniline.

Depending on the color carrier mass used, in specific cases it is also possible to add anionic ("acidic") dyes compatible with the cationic dyes used, such as, for example, 6-hydroxy-5-[(4-sulfophenyl)azo]-2-naphthalenesulfonic acid disodium salt (CI15985; Food Yellow No. 3; FD&C Yellow No. 6), 2,4-dinitro-1-naphthol-7-sulfonic acid disodium salt (CI10316; Acid Yellow No. 1; Food Yellow No. 1), 2-(indane-1,3-dion-2-yl)quinoline-x,x-sulfonic acid (mixture of mono- and disulfonic acid) (CI47005; D&C Yellow No. 10; Food Yellow No. 13, Acid Yellow No. 3), 5-hydroxy-1-(4-sulfophenyl)-4-[(4-sulfophenyl)azo]pyrazole-3-carboxylic acid trisodium salt (CI19140; Food Yellow No. 4; Acid Yellow No. 23), 9-(2-carboxyphenyl)-6-hydroxy-3H-xanthen-3-one (CI45350; Acid Yellow No. 73; D&C Yellow No. 8), 4-((4-amino-3-sulfophenyl)azo)benzenesulfonic acid disodium salt (CI13015, Acid Yellow No. 9), 5-[(2,4-dinitrophenyl)amino]-2-phenylaminobenzenesulfonic acid sodium salt (CI10385; Acid Orange No. 3), 4-[(2,4-dihydroxyphenyl)azo]benzenesulfonic acid monosodium salt (CI14270; Acid Orange No. 6), 4-[(2-hydroxynaphth-1-yl)azo]benzenesulfonic acid sodium salt (CI15510; Acid Orange No. 7), 4-((2-hydroxynaphthalen-1-yl)azo)-3-methylbenzenesulfonic acid sodium salt (CI15575; Acid Orange No. 8), 4-[(2,4-dihydroxy-3-[(2,4-dimethylphenyl)azo]phenyl)azo]benzenesulfonic acid sodium salt (CI20170; Acid Orange No. 24), 3',6'-dihydroxy-4',5'-diiodospiro(isobenzofuran-1(3H)-9'-(9H)xanthen)-3-one (CI45425, D&C Orange No. 10), 4-hydroxy-3-[(4-sulfonaphth-1-yl)azo]-1-naphthalenesulfonic acid disodium salt (CI14720; Acid Red No. 14), 4-hydroxy-3-[(2-methoxyphenyl)azo]-1-naphthalenesulfonic acid monosodium salt (CI14710; Acid Red No. 4), 6-hydroxy-5-[(4-sulfonaphth-1-yl)azo]-2,4-naphthalenedisulfonic acid trisodium salt (CI16255; Ponceau 4R; Acid Red No. 18), 3-hydroxy-4-[(4-sulfonaphth-1-yl)azo]-2,7-naphthalenedisulfonic acid trisodium salt (CI16185; Acid Red No. 27), 8-amino-1-hydroxy-2-(phenylazo)-3,6-naphthalenedisulfonic acid disodium salt (CI17200; Acid Red No. 33), 5-(acetylamino)-4-hydroxy-3-[(2-methylphenyl)azo]-2,7-naphthalenedisulfonic acid disodium salt (CI18065; Acid Red No. 35), 2-(3-hydroxy-2,4,5,7-tetraiododibenzopyran-6-on-9-yl)benzoic acid disodium salt (CI45430; Acid Red No. 51), N-[6-(diethylamino)-9-(2,4-disulfophenyl)-3H-xanthen-3-ylidene]-N-ethylethaneammonium hydroxide, internal salt, sodium salt (CI45100; Acid Red No. 52), 8-[(4-(phenylazo)phenyl)azo]-7-naphthol-1,3-disulfonic acid disodium salt (CI27290; Acid Red No. 73), 2',4',5',7'-tetrabromo-3',6'-dihydroxyspiro[isobenzofuran-1(3H), 9'-[9H]xanthen]-3-one disodium salt (CI45380; Acid Red No. 87), 2',4',5',7'-tetrabromo-4,5,6,7-tetrachloro-3',6'-dihydroxyspiro[isobenzofuran-1(3H), 9'[9H]xanthen]-3-one disodium salt (CI45410; Acid Red No. 92), 3',6'-dihydroxy-4',5'-diiodospiro[isobenzofuran-1(3H), 9'(9H)-xanthen]-3-one disodium salt (CI45425; Acid Red No. 95), 2-hydroxy-3-((2-hydroxynaphth-1-yl)azo)-5-nitrobenzenesulfonic acid monosodium salt (CI5685; Acid Red No. 184), (2-sulfophenyl)di[4-(ethyl((4-sulfophenyl)methyl)amino)phenyl]carbenium disodium salt, betaine (CI42090; Acid Blue No. 9; FD&C Blue No. 1), 3-hydroxy-4-((4-methyl-2-sulfophenyl)azo)-2-naphthalenecarboxylic acid disodium salt (CI15850; D&C Red No. 6), 6-hydroxy-5-((2-methoxy-5-methyl-4-sulfophenyl)azo)-2-naphthalenesulfonic acid disodium salt (CI16035; FD&C Red 40), 1,4-bis[(2-sulfo-4-methylphenyl)amino]-9,10-anthraquinone disodium salt (CI61570; Acid Green No. 25), bis[4-(dimethylamino)phenyl]-(3,7-disulfo-2-hydroxynaphth-1-yl)carbenium internal salt, monosodium salt (CI44090; Food Green No. 4; Acid Green No. 50), bis[4-(diethylamino)phenyl](2,4-disulfophenyl)carbenium internal salt, sodium salt (2:1) (CI42045; Food Blue No. 3; Acid Blue No. 1), bis[4-(diethylamino)phenyl](5-hydroxy-2,4-disulfophenyl)carbenium internal salt, calcium salt (2:1) (CI42051; Acid Blue No. 3), 1-amino-4-(cyclohexylamino)-9,10-anthraquinone-2-sulfonic acid sodium salt (CI62045; Acid Blue No. 62), 3,3-bis(3,5-dibromo-4-hydroxyphenyl)-4,5,6,7-tetrabromo-2,1(3h)-benzoxathiol 1,1-dioxide, 1-amino-4-(phenylamino)-9,10-anthraquinone-2-sulfonic acid (CI62055; Acid Blue No. 25), 2-(1,3-dihydro-3-oxo-5-sulfo-2H-indol-2-ylidene)-2,3-dihydro-3-oxo-1H-indole-5-sulfonic acid disodium salt (CI73015; Acid Blue No. 74), 9-(2-carboxyphenyl)-3-[(2-methylphenyl)amino]-6-[(2-methyl-4-sulfophenyl)amino]xanthylium internal salt, monosodium salt (CI45190; Acid Violet No. 9), 1-hydroxy-4-[(4-methyl-2-sulfophenyl)amino]-9,10-anthraquinone sodium salt (CI60730; D&C Violet No. 2; Acid Violet No. 43), bis[3-nitro-4-[(4-phenylamino)-3-sulfophenylamino]phenyl]sulfone (CI10410; Acid Brown No. 13), 5-amino-4-hydroxy-6-[(4-nitrophenyl)azo]-3-(phenylazo)-2,7-naphthalenedisulfonic acid disodium salt (CI20470; Acid Black No. 1), 3-hydroxy-4-[(2-hydroxynaphth-1-yl)azo]-7-nitro-1-naphthalenesulfonic acid-chromium complex (3:2) (CI5711; Acid Black No. 52), 3-[(2,4-dimethyl-5-sulfophenyl)azo]-4-hydroxy-1-naphthalenesulfonic acid disodium salt (CI14700; Food Red No. 1; Ponceau SX; FD&C Red No. 4), 4-(acetylamino)-5-hydroxy-6-[(7-sulfo-4-[(4-sulfo-phenyl)azo]naphth-1-yl)azo]-1,7-naphthalenedisulfonic acid tetrasodium salt (CI28440; Food Black No. 1), 3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195).

The total content of additional natural and/or synthetic nonoxidative dyes in the colorant according to the invention is about 0.01 to 15 percent by weight, in particular about 0.1 to 12 percent by weight.

Oxidative dye precursors, such as, for example, paraphenylenediamines, metaphenylenediamines, aminophenols or 4,5-diaminopyrazoles, can of course also be added to the colorant according to the invention.

The additional developer substances and coupler substances may be present in the colorant in each case in a total amount of from about 0.01 to 20 percent by weight, preferably about 0.1 to 10 percent by weight and in particular 0.1 to 5 percent by weight.

To increase the color intensity, carriers customary in cosmetic systems can be added if required. Suitable compounds are described, for example, in DE-A 196 18 595, to which reference is hereby expressly made. Particularly suitable carriers are, for example, benzyl alcohol, vanillin and isovanillin.

The dyes described above are applied for the coloring in a suitable color carrier mass.

The preparation form of the colorant according to the invention can, for example, be a solution, in particular an aqueous or aqueous-alcoholic solution. The particularly preferred preparation forms are, however, a cream, a gel, an emulsion or a powder or a granule preparation. Its composition is a mixture of the dyes with the additives customary for such preparations.

Customary additives in solutions, creams, emulsions, gels, powders or granules are, for example, solvents, such as water, lower aliphatic alcohols, for example ethanol, propanol or isopropanol, glycerol or glycols, such as 1,2-propylene glycol, and also wetting agents or emulsifiers from the classes of anionic, cationic, amphoteric or nonionogenic surface-active substances, such as, for example, fatty alcohol sulfates, oxyethylated fatty alcohol sulfates, alkylsulfonates, alkylbenzenesulfonates, alkyltrimethylammonium salts, alkylbetaines, oxyethylated fatty alcohols, oxyethylated nonylphenols, fatty acid alkanolamides and oxyethylated fatty acid esters, also thickeners such as higher fatty alcohols, starch, cellulose derivatives, petrolatum, paraffin oil, sugars and fatty acids, and also care substances, such as cationic resins, cationic, nonionic, anionic and amphoteric polymers, lanolin derivatives, cholesterol, pantothenic acid and betaine. The constituents mentioned are used in the amounts customary for such purposes, for example the wetting agents and emulsifiers in concentrations of from about 0.1 to 30 percent by weight, the The ready-to-use composition has a pH of from 2 to 11, preferably a pH of from 5 to 11. An alkaline pH is established here preferably using ammonia, although it is also possible to use organic amines, for example 2-amino-2-methyl-1-propanol, tris(hydroxymethyl)aminomethane, monoethanolamine and triethanolamine, or mixtures of organic amines and ammonia, and inorganic bases, such as sodium hydroxide and potassium hydroxide. Excessively high pH values can be corrected with inorganic or organic acids, for example phosphoric acid, acetic acid, lactic acid, ascorbic acid, citric acid or tartaric acid.

An amount sufficient for the coloring treatment, generally about 60 to 200 grams, neat or of the mixture is then applied to the keratin fibers and the coloring preparation is left to act at about 15 to 50° C., preferably 30 to 40° C., for about 10 to 45 minutes, preferably 30 minutes, then the keratin fibers are rinsed with water and dried. If required, this rinsing is followed by washing with a shampoo and possibly after-rinsing with a weak organic acid, such as, for example, citric acid or tartaric acid. The keratin fibers are then dried.

The colorant with a content of cationic azacyanine dyes of the formula (I) permits, inter alia, a simple and gentle coloration of hair with varying degrees of damage (for example recolorations of sections of hair which have already been oxidatively colored), the color carrier mass without oxidizing agent—neat or mixed with an acidic, neutral or basic aqueous diluent—being applied to the predamaged sections of hair (for example the hair ends), while the color carrier mass mixed with the oxidizing agent is applied to the sections of hair with little or no predamage (for example the new hair growth). The aqueous component used for dilution can comprise the abovementioned customary additives for solutions, creams, emulsions or gels. This process allows colorations matched to the nature of the hair which are characterized by a hair-gentle evening out between roots and ends, which is not possible when using customary oxidative hair colorants since an oxidizing agent is always required to couple the dye precursors. thickeners in an amount of from about 0.1 to 30 percent by weight and the care substances in a concentration of from about 0.1 to 5.0 percent by weight.

Moreover, further customary additives, for example antioxidants, such as ascorbic acid, thioglycolic acid or sodium sulfite, and also perfume oils, penetration agents, buffer systems, complexing agents, preservatives, wetting agents, emulsifiers, thickeners, encapsulation media, granulation auxiliaries and care substances may also be present in the colorant.

The ready-to-use colorant according to the invention can be applied neat or be prepared directly prior to use by mixing the color carrier mass comprising the dyes with water, a care product or with an oxidizing agent.

Suitable oxidizing agents are primarily hydrogen peroxide or its addition compounds onto urea, melamine, sodium borate or sodium carbonate in the form of a 1- to 12-percent strength, preferably a 3- to 6-percent strength, aqueous solution. For compositions with simultaneous lightening or bleaching, depending on the dye of the formula (I) used, it is also additionally possible to add persulfates, e.g. ammonium persulfate, potassium persulfate or sodium persulfate. The weight ratio between color carrier mass and oxidizing agent here is preferably about 5:1 to 1:3, in particular 1:1 to 1:2. Relatively large amounts of oxidizing agents are used primarily with relatively high concentrations of oxidative dye precursors in the colorant, or if a relatively strong bleaching of the keratin fibers (in particular of hair) is intended at the same time.

The pH of the ready-to-use colorant according to the invention can be adjusted such that it can be applied neat or, upon mixing the color carrier mass with a diluent (conditioner, water, etc.) or the oxidizing agent, it adjusts to a pH which is determined by the pH of the color carrier mass and of the diluent or of the oxidizing agent, and also by the mixing ratio.

The colorant according to the invention is characterized by colorations with good color intensity and brilliance, a good evening out of color between damaged and undamaged hair (such as, for example, between hair ends and new hair growth), good durability, very good mildness to the hair and variable application options with and without oxidizing agents.

The examples below are intended to illustrate the subject-matter in more detail without limiting it to these examples.

EXAMPLES

Example 1

Preparation of 2-[(1-ethyl-4(1H)-quinolinylidene)amino]-6-methoxy-3-methyl-1,3-benzothiazol-3-ium tetrafluoroborate (dye of the Formula (III))

0.38 g (2 mmol) of 6-methoxy-3-methylbenzothiazolon-(2)-imine are dissolved in 10 ml of acetonitrile under nitrogen. 0.56 g (2 mmol) of 4-chloro-1-ethylquinolinium tetrafluoroborate is added. After 30 minutes under reflux, the mixture is left to cool and filtered. The filtrate is concentrated by evaporation, and the combined residues are suspended in water, filtered, washed with water and dried. This gives 0.34 g (40% of theory) of an orange-colored solid.

$^1$H-NMR (DMSO-d$_6$) δ=1.5 (t, 3H); 3.8 (s, 3H); 3.9 (s, 3H); 4.8 (q, 2H); 7.2 (m, 1H); 7.6 (m, 3H); 7.8 (m, 1H); 8.1 (m, 1H); 8.3 (m, 1H); 8.8 (m, 1H); 9.0 (m, 1H).

Example 2

Hair Colorant with Symmetrical Dye

| | |
|---|---|
| 6-Methoxy-2-[(6-methoxy-3-methyl-1,3-benzothiazol-2(3H)-ylidene)amino]-3-methyl-1,3-benzothiazol-3-ium 4-methylbenzenesulfonate (Dye of the formula II) | 2.0 g |
| Ethanol | 30.0 g |
| Cetyltrimethylammonium chloride | 0.5 g |
| Water, demineralized | ad 100.0 g |

The pH is adjusted to 10 using 25% strength ammonia.

5 g of the above color carrier mass are mixed with 5 g of a 6% strength hydrogen peroxide solution. The resulting ready-to-use hair colorant is applied to bleached hair and distributed evenly using a brush. After a contact time of 20 minutes at 40° C., the hair is rinsed with lukewarm water, washed with a shampoo, rinsed with lukewarm water and then dried. This gives a cold yellow coloration.

Example 3

Hair Colorant with Symmetrical Dye

| | |
|---|---|
| 6-Methoxy-2-[(6-methoxy-3-methyl-1,3-benzothiazol-2(3H)-ylidene)amino]-3-methyl-1,3-benzothiazol-3-ium 4-methylbenzenesulfonate (Dye of the formula II) | 2.0 g |
| Ethanol | 30.0 g |
| Cetyltrimethylammonium chloride | 0.5 g |
| Water, demineralized | ad 100.0 g |

The pH is adjusted to 7.5 using 25% strength ammonia.

5 g of the above color carrier mass are mixed with 5 g of a cationic conditioner. The resulting ready-to-use hair colorant is applied to bleached hair and distributed evenly using a brush. After a contact time of 20 minutes at 40° C., the hair is rinsed with lukewarm water, washed with a shampoo, rinsed with lukewarm water and then dried. This gives a cold yellow coloration.

Example 4

Hair Colorant with Symmetrical Dye

| | |
|---|---|
| 8H-Diisoquinolino[1,2-a:2',1'-d][1,3,5]triazin-5-ium iodide (Dye of the formula (IV)) | 2.0 g |
| Ethanol | 30.0 g |
| Laureth-4 | 0.5 g |
| Water, demineralized | ad 100.0 g |

The pH is adjusted to 10 using 25% strength ammonia.

5 g of the above color carrier mass are mixed with 5 g of a 6% strength hydrogen peroxide solution. The resulting ready-to-use hair colorant is applied to bleached hair and distributed evenly using a brush. After a contact time of 20 minutes at 40° C., the hair is rinsed with lukewarm water, washed with a shampoo, rinsed with lukewarm water and then dried.

This gives an intense, warm yellow coloration.

Example 5

Hair Colorant with Symmetrical Dye

| | |
|---|---|
| 8H-Diisoquinolino[1,2-a:2',1'-d][1,3,5]triazin-5-ium iodide (Dye of the formula (IV)) | 2.0 g |
| Ethanol | 30.0 g |
| Laureth-4 | 0.5 g |
| Ammonium persulfate | 5.0 g |
| Water, demineralized | ad 100.0 g |

The pH is adjusted to 10 using 25% strength ammonia.

5 g of the above color carrier mass are mixed with 5 g of a 6% strength hydrogen peroxide solution. The resulting ready-to-use hair colorant is applied to dark blond hair and distributed evenly using a brush. After a contact time of 20 minutes at 40° C., the hair is rinsed with lukewarm water, washed with a shampoo, rinsed with lukewarm water and then dried. This gives an intense, warm yellow coloration.

Example 6

Hair Colorant with Symmetrical Dye

| | |
|---|---|
| 8H-Diisoquinolino[1,2-a:2',1'-d][1,3,5]triazin-5-ium iodide (Dye of the formula (IV)) | 1.0 g |
| Ethanol | 30.0 g |
| Laureth-4 | 0.5 g |
| Water, demineralized | ad 100.0 g |

The pH is adjusted to 5.0 using 25% strength ammonia.

10 g of the above color carrier mass are applied to bleached hair and distributed evenly using a brush. After a contact time of 20 minutes at 40° C., the hair is rinsed with lukewarm water, washed with a shampoo, rinsed with lukewarm water and then dried. This gives an intense, warm yellow coloration.

Example 7

Hair Colorant with Asymmetrical Dye

| | |
|---|---|
| 2-[(1-Ethyl-4(1H)-quinolinylidene)amino]-6-methoxy-3-methyl-1,3-benzothiazol-3-ium tetrafluoroborate (dye of the formula (III)) | 2.0 g |
| Ethanol | 30.0 g |
| Laureth-4 | 0.5 g |
| Water, demineralized | ad 100.0 g |

The pH is adjusted to 9.5 using 25% strength ammonia.

5 g of the above color carrier mass are mixed with 5 g of a 6% strength hydrogen peroxide solution. The resulting ready-to-use hair colorant is applied to bleached hair tresses and distributed evenly using a brush. After a contact time of 20 minutes at 40° C., the hair is rinsed with lukewarm water, washed with shampoo, rinsed with lukewarm water and then dried. This gives an intense, warm yellow coloration.

Example 8

Oxidation Hair Colorant (Multicomponent Kit)

| Dye pellets prepared in the top-spray process (component A) | |
| --- | --- |
| 2.40 g | 1-hydroxyethyl-4,5-diaminopyrazole sulfate |
| 1.23 g | 4-Amino-2-hydroxytoluene |
| 1.00 g | 2-[(1-Ethyl-4(1H)-quinolinylidene)amino]-6-methoxy-3-methyl-1,3-benzothiazol-3-ium tetrafluoroborate (dye of the formula (III)) |
| 3.00 g | Ascorbic acid |
| 1.00 g | Ethylenediaminotetraacetate disodium salt |
| 50.00 g | Gum Arabic, 20% strength solution in water |
| 6.43 g | Hydrogenated saccharides (6-O-α-glucopyranolyl-D-sorbitol and 1-O-α-glucopyranolyl-D-mannitol) |

In the preparation of dye pellets in the top-spray process in a Glatt fluidized-bed granulator and coater, the fill material (hydrogenated saccharides) is initially introduced and heated to a product temperature of about 34° C. at an air inlet temperature of 75° C. and an amount of air of 55-65 m3/h. A dye dispersion comprising the remaining constituents ("spray solution") is then sprayed onto the initially introduced fill material at an initial spraying rate of 15-22 g/min and a spray-air pressure of 1.2-1.4 bar. In the course of the granulation process, the spraying rate and the air inlet temperature are kept constant. The amount of air is increased to a maximum of 100 m3/h. The product temperature is maintained between 40 and 60° C. throughout the entire process. After applying the dye dispersion, the pellets are dried at a maximum product temperature of 60° C., then cooled to about 30° C. and sieved.

| Cream base (component B) | |
| --- | --- |
| 8.70 g | Cetylstearyl alcohol |
| 2.30 g | Glyceryl stearate (self-emulsifying) |
| 0.80 g | Lanolin |
| 3.80 g | Lanolin alcohol |
| 1.42 g | Steareth-20 |
| 0.07 g | Formaldehyde |
| 0.01 g | Tocopherol |
| 0,20 g | Perfume |
| 10.00 g | Ammonia (25% strength aqueous solution) |
| ad 100.00 g | Water |
| Hydrogen peroxide emulsion (component C) | |
| 9.00 g | Hydrogen peroxide |
| 1.80 g | Cetylstearyl alcohol |
| 3.30 g | Polyvinylpyrrolidone/styrene copolymer |
| 0.20 g | Disodium phosphate |
| 0.20 g | Steareth-20 |
| 0.10 g | Salicylic acid |
| 0.08 g | Phosphoric acid |
| ad 100.00 g | Water |

The hydrogen peroxide emulsion above is prepared in the classic hot emulsifying process.

Directly prior to application, 6 g of this hydrogen peroxide emulsion (component C) are mixed with 6 g of the cream base (component B) and 0.6 g of dye pellets (component A) in a coloring dish or shaking bottle. The resulting ready-to-use hair colorant is applied to pale brown hair and distributed evenly using a brush. After a contact time of 20 minutes at 40° C., the hair is rinsed with lukewarm water, washed with shampoo, rinsed with lukewarm water and then dried. An intense orange coloration is obtained.

Unless stated otherwise, all of the percentages in the present application are percentages by weight.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An agent for the nonoxidative coloring of keratin fibers, comprising at least one cationic azacyanine dye of the general formula (I);

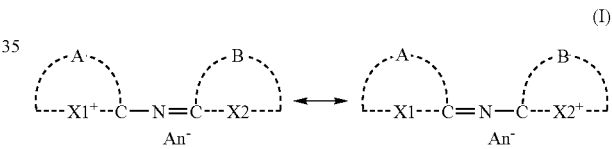

where X1 is N—R1, O or S and X2 is N—R2, O or S;
A and B are the group required to form an aromatic carbocyclic or heterocyclic (nitrogen, oxygen or sulfur, where up to three heteroatoms may be present), 5- or 6-membered ring to which further carbocyclic or heterocyclic 5- or 6-membered rings may be fused;
R1 and R2 independently of one another, may be identical or different and are a substituted or unsubstituted, saturated or unsaturated (C1-C10)-alkyl group, a substituted or unsubstituted aryl group or a substituted or unsubstituted benzyl group, or act as a member of a fused carbocyclic or heterocyclic 5- or 6-membered ring; and
An⁻ is an anion;
wherein the azacyanine dye of said formula (I) is chosen from,
6-methoxy-2-[(6-methoxy-3-methyl-1,3-benzothiazol-2 (3H)-ylidene)amino]-3-methyl-1,3-benzothiazol-3-ium 4-methylbenzenezenesulfonate,
8 H-diisoquinolino[1,2-a:2',1'-][1,3,5]triazin-5-ium iodide,
2-[(1-ethyl-4(1H)-quinolinylidene)amino]-6-methoxy-3-methyl-1,3-benzothiazol-3-ium tetrafluoroborate, 2-{[-1-ethylquinolinylidene]amino}-6-methoxy-3-methyl-1,3-benzothiazol-3-ium iodide,
2-{[-1-ethylquinolinylidene]amino}-6-methoxy-3-methyl-1,3-benzothiazol-3-ium bromide, 1-ethyl-4-{[1-ethylquinolinylidene]amino}quinolinium cloride, 1-ethyl-4-[(1-ethyl-4(1H)-quinolinylidend)amino]quino-linium chloride,
1-ethyl-4-{[1-ethylquinolinylidene]amino}quinolinium chloride,
1-ethyl-4-[2H-quinolizin-2-ylidenamino]quinolinium chloride,
6-methoxy-3-methyl-2-[2H-quinolizin-2-ylidenamino]-1,3-benzothiazol-3-ium acetate, 4-(4H-thiochromen-4-ylidenamino)thiochromenium chloride,
4-{[ethylquinolinylidene]amino}chromenium chloride, 1-[1H-isochromen-1-ylidenamino]ischromenium iodide, 2-[(1-ethyl-4-(1H)-quinolinylidene)amino]-3-methyl-1,3-thiazol-3-ium ethylsulfate,
2-[(1-ethyl-4(1H)-quinolinylidene)amino]-3-methyl-1,3-thiazol-3-ium tetrafluoroborate, 2-[(1-ethyl-4-(1H) quinolinylidene)amino]-3,5-dimethyl-1,3-thiazol-3-ium ethylsulfate, 2-[(1-ethyl-4-(1H)-quinolinylidene) amino]-3,4-dimethyl-1,3-thiazol-3-ium ethylsulfate, and 2-[(1-ethyl-4-(1H)-quinolinylidene)amino]-3,4,5-trimethyl-1,3-thiazol-3-ium ethylsulfate.

2. An agent according to claim 1, wherein the azacyanine dye of said formula (I) is present in a total amount of from 0.01 to 15% by weight.

3. An agent according to claim 1, wherein said agent is a hair colorant.

4. A method of coloring hair with varying degrees of damage where the color carrier mass comprising the azacyanine dye of the formula (I) according to claim 1 without oxidizing agent—neat or mixed with an acidic, neutral or basic aqueous diluent—is applied to the predamaged sections of hair while the color carrier mass mixed with the oxidizing agent is applied to the sections of hair with little or no predamage.

* * * * *